(12) United States Patent
Assef et al.

(10) Patent No.: US 10,836,691 B2
(45) Date of Patent: Nov. 17, 2020

(54) UPGRADING A C5 OLEFIN STREAM

(71) Applicant: FINA TECHNOLOGY, INC., Houston, TX (US)

(72) Inventors: James Assef, Pearland, TX (US); Scott Cooper, Humble, TX (US); Kaushik Gandhi, League City, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 68 days.

(21) Appl. No.: 14/861,316

(22) Filed: Sep. 22, 2015

(65) Prior Publication Data

US 2017/0081260 A1    Mar. 23, 2017

(51) Int. Cl.
| | | |
|---|---|---|
| *C07C 7/10* | (2006.01) | |
| *C07C 5/327* | (2006.01) | |
| *B01D 3/40* | (2006.01) | |
| *C10G 21/00* | (2006.01) | |
| *C10G 35/00* | (2006.01) | |
| *C10G 61/04* | (2006.01) | |

(52) U.S. Cl.
CPC ................. *C07C 7/10* (2013.01); *B01D 3/40* (2013.01); *C07C 5/327* (2013.01); *C10G 21/00* (2013.01); *C10G 35/00* (2013.01); *C10G 61/04* (2013.01); *C10G 2300/4081* (2013.01); *C10G 2400/22* (2013.01)

(58) Field of Classification Search
CPC .......................................... C07C 5/327–3337
See application file for complete search history.

(56) References Cited

U.S. PATENT DOCUMENTS

| | | | | | |
|---|---|---|---|---|---|
| 2,458,082 | A | * | 1/1949 | Kilpatrick | C07C 5/3332 585/627 |
| 2,459,403 | A | * | 1/1949 | Ahrens | C07C 7/005 203/54 |
| 2,993,841 | A | * | 7/1961 | Sarno | C07C 7/08 203/51 |
| 3,230,157 | A | * | 1/1966 | Hill | C07C 7/04 203/53 |
| 3,660,513 | A | * | 5/1972 | Davison | C07C 5/277 585/326 |
| 3,784,626 | A | * | 1/1974 | Ginnasi | C07C 7/08 203/53 |

(Continued)

*Primary Examiner* — In Suk C Bullock
*Assistant Examiner* — Alyssa L Cepluch
(74) *Attorney, Agent, or Firm* — Albert Shung (57) ABSTRACT

A process is provided including subjecting a raw $C_5$ stream containing $C_5$ diolefins to extractive distillation to form $C_5$ diolefins and a raffinate stream. The process includes subjecting the raffinate stream to dehydrogenation to form additional $C_5$ diolefins, which are recycled to the extractive distillation. Another process includes modifying a $C_5$ diolefin extractive distillation unit by forming a recycle loop with a $C_5$ olefin dehydrogenation reactor. A system is provided that includes a $C_5$ diolefin extractive distillation unit and a $C_5$ olefin dehydrogenation reactor that are arranged in a recycle loop. A process is provided that includes subjecting a raffinate stream containing $C_5$ olefins from an extractive distillation unit to dehydrogenation to form $C_5$ diolefins.

14 Claims, 5 Drawing Sheets

(56) References Cited

U.S. PATENT DOCUMENTS

| | | | | |
|---|---|---|---|---|
| 3,851,010 A | * | 11/1974 | Rescalli | ................. C07C 7/005 |
| | | | | 203/51 |
| 4,140,587 A | * | 2/1979 | Paret | ................. B01D 11/0426 |
| | | | | 203/58 |
| 4,310,388 A | * | 1/1982 | Volkamer | ................. C07C 7/08 |
| | | | | 203/51 |
| 7,696,395 B2 | | 4/2010 | Merrill | |
| 2010/0022816 A1 | | 1/2010 | Merrill | |

* cited by examiner

UPGRADING A C5 OLEFIN STREAM

CROSS-REFERECNE TO RELATED APPLICATIONS

Not applicable.

FIELD

Embodiments of the present disclosure generally relate to production of diolefins. More particularly, embodiments relate to increasing production of $C_5$ diolefins in an extractive distillation process.

BACKGROUND

One method of obtaining diolefins, such as $C_4$ or $C_5$ diolefins, includes extractive distillation of a cut from a hydrocarbon cracking process, such as steam cracking or catalytic cracking, containing diolefins. A "cut" as used herein refers to a portion of an original stream separated by traditional processing equipment, including, but not limited to distillation. A "distillation cut" refers specifically to a portion of an original stream separated from the original stream by a distillation process. Extractive distillation, also referred to as fractional extraction or solvent extraction, involves altering relative volatilities of compounds by addition of a solvent for separation thereof via distillation.

Use of lighter cracker feedstocks reduces the availability of cuts formed during cracking that contain $C_5$ diolefins, destabilizing available supply of $C_5$ diolefins for other uses.

SUMMARY

The present disclosure provides for a process. The process includes subjecting a raw $C_5$ stream containing $C_5$ diolefins to extractive distillation in an extractive distillation unit to form distillation cuts containing $C_5$ diolefins and a raffinate stream containing $C_5$ olefins. The process includes removing the distillation cuts from the extractive distillation unit. The process includes subjecting at least a portion of the raffinate stream to dehydrogenation in a dehydrogenation reactor to form a dehydrogenation product stream containing $C_5$ diolefins. The process includes recycling the dehydrogenation product stream to the extractive distillation unit.

The present disclosure provides for a process for modifying a $C_5$ diolefin extractive distillation unit. The process includes providing a $C_5$ olefin dehydrogenation reactor. The process includes forming a recycle loop with the $C_5$ olefin dehydrogenation reactor and the $C_5$ diolefin extractive distillation unit.

The present disclosure provides for a system. The system includes a $C_5$ diolefin extractive distillation unit. The system includes a $C_5$ olefin dehydrogenation reactor. The $C_5$ olefin dehydrogenation reactor and the $C_5$ diolefin extractive distillation unit are arranged to form a recycle loop.

A process is provided that includes subjecting at least a portion of a raffinate stream containing $C_5$ olefins from an extractive distillation unit to dehydrogenation in a dehydrogenation reactor to form a dehydrogenation product stream containing $C_5$ diolefins.

BRIEF DESCRIPTION OF DRAWINGS

The present disclosure may be understood from the following detailed description when read with the accompanying figures.

DETAILED DESCRIPTION

A detailed description will now be provided. The following disclosure includes specific embodiments, versions and examples, but the disclosure is not limited to these embodiments, versions or examples, which are included to enable a person having ordinary skill in the art to make and use the disclosure when the information in this application is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Figure 1:
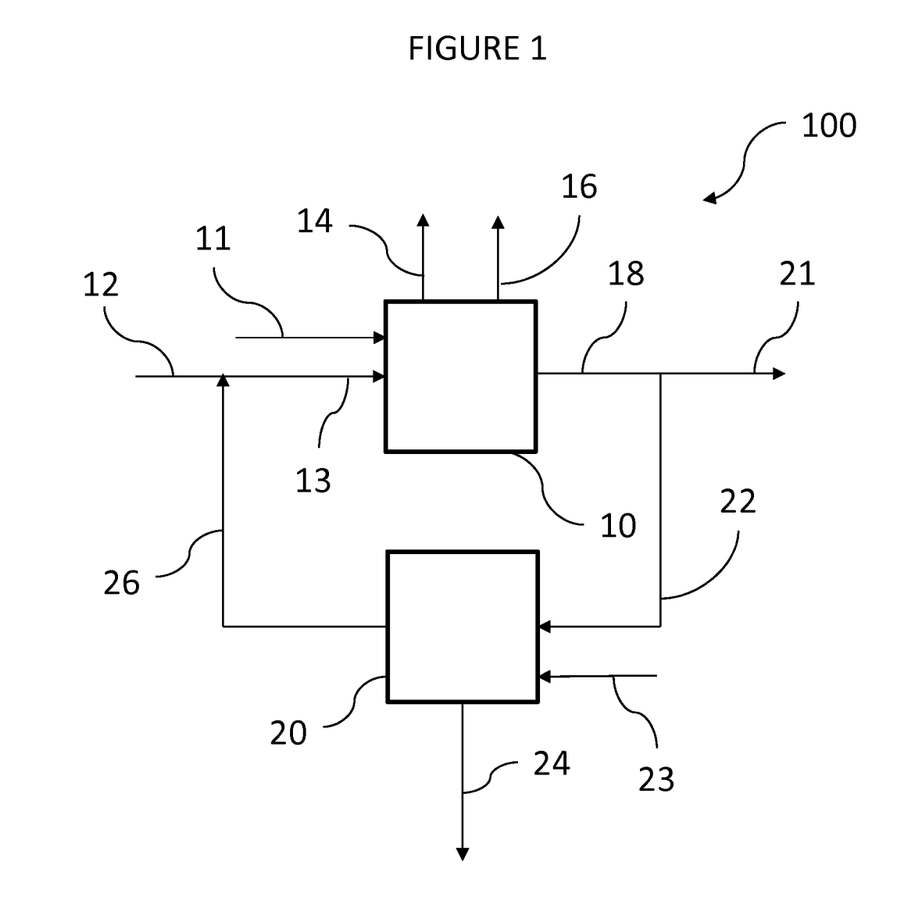
FIG. 1 depicts a process flow diagram in accordance with certain embodiments of the present disclosure.

Certain embodiments of the present disclosure relate to a process for increasing an amount of $C_5$ diolefin obtained from a raw $C_5$ stream. With reference to FIG. 1, the process may include subjecting raw $C_5$ stream 12 to extractive distillation in $C_5$ diolefin extractive distillation unit 10 of system 100. "Extractive distillation unit" as used herein may be one or more extractive distillation columns. In embodiments with multiple extractive distillation columns, the extractive distillation columns may be arranged in series.

Raw $C_5$ stream 12 may contain $C_5$ diolefins, $C_5$ olefins, paraffins, naphthenes, diolefins other than $C_5$ diolefins, olefins other than $C_5$ olefins, or combinations thereof. In some embodiments, raw $C_5$ stream 12 is a cut taken from a crude $C_{5+}$ stream separated from a cracker effluent (e.g., by fractional distillation). Raw $C_5$ stream 12 may be separated from such a crude $C_{5+}$ stream by fractional distillation, for example. Crude $C_{5+}$ stream may include diolefins, olefins, paraffins, or combinations thereof, each having 5 or more carbon atoms. Raw $C_5$ stream 12 may include diolefins, olefins, paraffins, or combinations thereof, each having 5 carbon atoms. For example and without limitation, the $C_5$ diolefins may include isoprene (also referred to as 2-methyl-1,3-butadiene), piperylene (also referred to as 1,3-pentadiene), cyclopentadiene (also referred to as cyclopenta-1,3-diene), or combinations thereof. The $C_5$ olefins may include isoamylene (also referred to as 2-methly but-2-ene), isopentene (including 2-methylbut-1-ene and 3-methylbut-1-ene), 1-pentene, cis-2-pentene, trans-2-pentene, or combinations thereof.

In some embodiments, raw $C_5$ stream 12 is a cut from a cracking process, such as thermal cracking or catalytic cracking of naphtha (e.g., light naphtha), crude oil, fuel oil, or gas oil. For example and without limitation, raw $C_5$ stream 12 may be pyrolysis gasoline.

Extractive distillation of raw $C_5$ stream 12 may be performed by methods known to those of ordinary skill in the art. For example and without limitation, in the extractive distillation of raw $C_5$ stream 12 a solvent 11, such as an aprotic polar solvent, having a high complexing affinity towards $C_5$ diolefins may be used. The solvent 11 may include acetonitrile, dimethylformamide, furfural, N-methyl-2-pyrrolidone, acetone, or dimethylacetamide, for example.

Extractive distillation of raw $C_5$ stream 12 may form one or more distillation cuts containing $C_5$ diolefins. The one or more distillation cuts may contain isoprene, piperylene, cyclopentadiene, or combinations thereof. For example and without limitation, extractive distillation of raw $C_5$ stream 12 may form first cut 14 containing isoprene, and second cut 16 containing piperylene. Such distillation cuts may be removed from $C_5$ diolefin extractive distillation unit 10. Subsequent to removal from $C_5$ diolefin extractive distillation unit 10, $C_5$ diolefin within each cut (e.g., first cut 14 and second cut 16) may be separated from solvent 11 within each cut. While not shown, separated solvent 11 from first cut 14 and/or second cut 16 may be recycled to $C_5$ diolefin extractive distillation unit 10.

First cut 14 and second cut 16 may contain a majority of a single $C_5$ diolefin isomer, such as isoprene or piperylene. For example, each cut may be greater than 50 percent by weight, greater than 60 percent by weight, greater than 70 percent by weight, greater than 80 percent by weight, greater than 90 percent by weight, greater than 95 percent by weight, greater than 99 percent by weight, or about 100 percent by weight of a single $C_5$ diolefin isomer.

$C_5$ diolefins exiting extractive distillation unit 10, such as first cut 14 and second cut 16, may be subsequently used as a feedstock in various processes known to those of ordinary skill in the art. For example and without limitation, $C_5$ diolefins may be used in resin manufacturing processes for the production of synthetic rubbers, plastics, and adhesives.

Extractive distillation of raw $C_5$ stream 12 may remove a majority of $C_5$ diolefins contained in raw $C_5$ stream 12 as distillation cuts, such as first cut 14 and second cut 16. For example and without limitation, greater than 50 weight percent, or greater than 60 weight percent, or greater than 70 weight percent, or greater than 80 weight percent, or greater than 90 weight percent, or greater than 95 weight percent, or greater than 99 weight percent, or about 100 weight percent (all by weight) of $C_5$ diolefins contained in raw $C_5$ stream 12 may exit $C_5$ diolefin extractive distillation unit 10 as top stream distillation cuts (e.g, first cut 14 and second cut 16).

Extractive distillation of raw $C_5$ stream 12 may form raffinate stream 18. Raffinate stream 18 may contain $C_5$ olefins, $C_5$ diolefins, paraffins, naphthenes, diolefins other than $C_5$ diolefins, olefins other than $C_5$ olefins, or combinations thereof.

The process may include subjecting at least a portion of raffinate stream 18 to dehydrogenation in $C_5$ olefin dehydrogenation reactor 20 to form dehydrogenation product stream 26. For example and without limitation, raffinate stream 18 may be separated into first portion of raffinate stream 21 and second portion of raffinate stream 22, such as by diverting a portion of raffinate stream 18. Raffinate stream 22 may include between 0 and 100 percent by weight of the flow of raffinate stream 18.

First portion of raffinate stream 21 may be purged from the process, such that only a portion of raffinate stream 18 is subjected to dehydrogenation in the $C_5$ olefin dehydrogenation reactor 20. First portion of raffinate stream 21 may contain paraffins, naphthenes, or combinations thereof.

Second portion of raffinate stream 22 may be sent to $C_5$ olefin dehydrogenation reactor 20. Second portion of raffinate stream 22 may contain $C_5$ olefins. In some embodiments, second portion of raffinate stream 22 is not a pure $C_5$ olefins stream. For example and without limitation, second portion of raffinate stream 22 may contain $C_5$ olefins, paraffins, naphthenes, $C_5$ diolefins, or combinations thereof. Second portion of raffinate stream 22 may contain less than 100 percent by weight, less than 90 percent by weight, less than 80 percent by weight, less than 70 percent by weight, less than 60 percent by weight, less than 50 percent by weight, less than 40 percent by weight, less than 30 percent by weight, less than 20 percent by weight, or less than 10 percent by weight of $C_5$ olefins.

Within $C_5$ olefin dehydrogenation reactor 20 the $C_5$ olefins in second portion of raffinate stream 22 may undergo dehydrogenation to form $C_5$ diolefins. One of ordinary skill in the art will recognize with the benefit of this disclosure that any number of traditional dehydrogenation processes may be used in dehydrogenation reactor 20. For instance, in one non-limiting embodiment, the dehydrogenation process used in dehydrogenation reactor 20 is described in U.S. Pat. No. 7,696,395, which is incorporated herein fully by reference. In some embodiments, paraffins in second portion of raffinate stream 22 may undergo dehydrogenation to form olefins within $C_5$ olefin dehydrogenation reactor 20. The olefins produced by dehydrogenation of paraffins may then be dehydrogenated to diolefins, such as in a subsequent pass through $C_5$ olefin dehydrogenation reactor 20 by flowing through the recycle loop. In certain embodiments, compounds in second portion of raffinate stream 22 may undergo cracking to lesser carbon number compounds including $C_4$ and $C_3$ compounds.

Dehydrogenation of second portion of raffinate stream 22 may form hydrogen and offgas stream 24. Dehydrogenation of second portion of raffinate stream 22 may form dehydrogenation product stream 26. Dehydrogenation product stream 26 may contain $C_5$ diolefins formed in $C_5$ olefin dehydrogenation reactor 20.

In certain embodiments, dehydrogenation of $C_5$ olefins to form $C_5$ diolefins may be performed in the presence of a catalyst. The catalyst may contain ferric oxide and potassium (e.g., potassium oxide or potassium carbonate), such as those disclosed in U.S. Patent No. 2010/0022816 and U.S. Pat. No. 7,696,395, which are incorporated herein by reference in their entireties. For example and without limitation, the catalyst may be STYROMAX® PLUS, commercially available from Sud-Chemie; or HYPERCAT™ (e.g., HYPERCAT™ GV), commercially available from CRI Catalyst Company; or FLEXICAT™ commercially available from CRI Catalyst Company; or ET11; or ASTROCAT. In some embodiments, the catalyst is a commercially available dehydrogenation catalyst, such as one available for dehydrogenation of butene to iso-butene, or isoamylene to isoprene, or ethylbenzene to styrene, for example.

In some embodiments, $C_5$ olefins are dehydrogenated to $C_5$ diolefins in the presence of a catalyst and oxygen. The oxygen may be provided to $C_5$ olefin dehydrogenation reactor 20 in the form of steam 23. For example and without limitation, a steam to hydrocarbon molar ratio within $C_5$ olefin dehydrogenation reactor 20 may be at least 10:1, at least 12:1, or at least 15:1.

In some embodiments, pressure within $C_5$ olefin dehydrogenation reactor 20 may be 1000 mbar or less, 850 or less, or 350 or less. Temperature within $C_5$ olefin dehydrogenation reactor 20 may be 300° C. or more, 500° C. or more, 600° C. or more, or from 300 to 800° C.

The process may include recycling dehydrogenation product stream 26 to $C_5$ diolefin extractive distillation unit 10. In certain embodiments, dehydrogenation product stream 26 may be processed in separations equipment (not shown) prior to being recycled to $C_5$ diolefin extractive distillation unit 10. For instance, methane and hydrogen in dehydrogenation product stream 26 through, in certain embodiments, stripping. Distillation may be used to remove compounds with higher or lower carbon numbers than $C_5$s. While recycling dehydrogenation product stream 26 to $C_5$ diolefin extractive distillation unit 10 is depicted as including combining dehydrogenation product stream 26 with raw $C_5$ stream 12 upstream of $C_5$ diolefin extractive distillation unit 10, one skilled in the art with the aid of this disclosure will recognize that dehydrogenation product stream 26 may be recycled to $C_5$ diolefin extractive distillation unit 10 in other ways. For example and without limitation, dehydrogenation product stream 26 and raw $C_5$ stream 12 may be separately fed into $C_5$ diolefin extractive distillation unit 10.

In some embodiments, a content of $C_5$ diolefins, by weight, of combined stream 13 is not less than a content of $C_5$ diolefins, by weight, in raw $C_5$ stream 12 alone (i.e., without combining raw $C_5$ stream 12 with dehydrogenation product stream 26). Combined stream 13 is a stream resulting from the combination of raw $C_5$ stream 12 and dehydrogenation product stream 26.

In some embodiments, the process results in production of more $C_5$ diolefins, by weight, than an otherwise identical process in which no portion of raffinate from extractive distillation is subjected to distillation to form $C_5$ diolefins. Thus, certain embodiments may increase availability of $C_5$ diolefins for use in subsequent processes, thereby stabilizing available supply of $C_5$ diolefins for use in such processes.

Figure 2A:
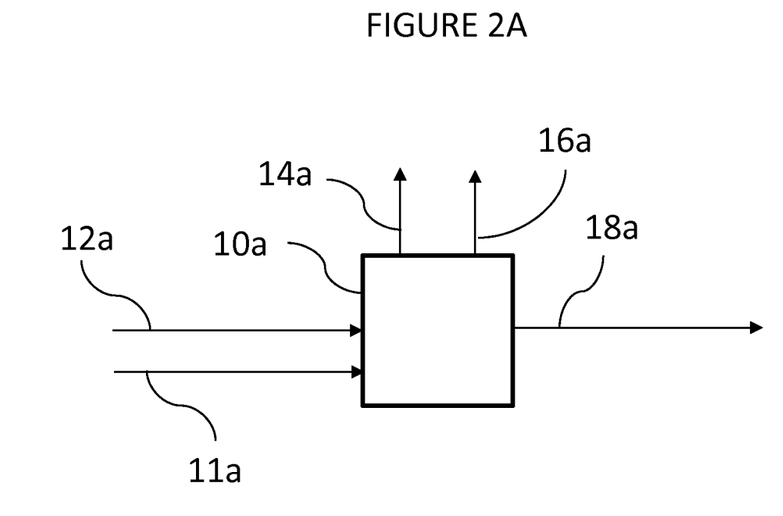
FIG. 2A depicts a extractive distillation unit in accordance with certain embodiments of the present disclosure.
Figure 2B:
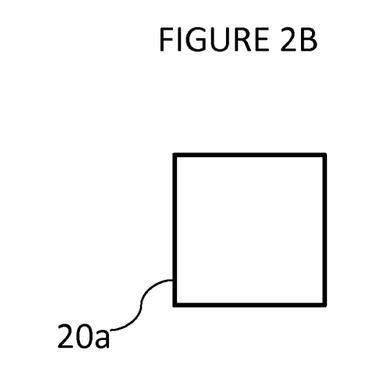
FIG. 2B depicts a dehydrogenation reactor in accordance with certain embodiments of the present disclosure.
Figure 2C:
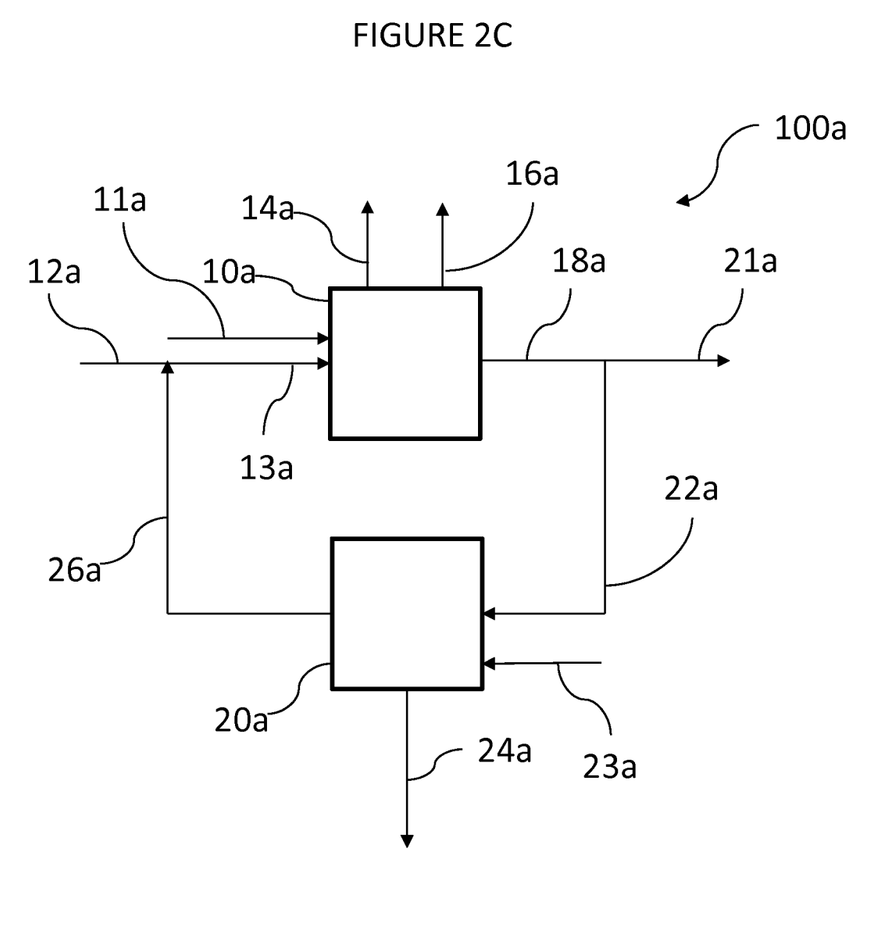
FIG. 2C depicts a modified extractive distillation unit formed by combining the extractive distillation unit of FIG. 2A with the dehydrogenation reactor of FIG. 2B in accordance with certain embodiments of the present disclosure.

Certain embodiments of the present disclosure relate to a process for modifying a $C_5$ diolefin extractive distillation unit for increasing an amount of $C_5$ diolefin obtained from a raw $C_5$ stream. With reference to FIGS. 2A-2C, the process may include providing a $C_5$ diolefin extractive distillation unit 10a, as depicted in FIG. 2A. $C_5$ diolefin extractive distillation unit 10a may be adapted for receiving raw $C_5$ stream 12a and subjecting raw $C_5$ stream 12a to extractive distillation in the presence of solvent 11a, as discussed above, to form first cut 14a, second cut 16a, and raffinate stream 18a.

The process may include providing $C_5$ olefin dehydrogenation reactor 20a, as depicted in FIG. 2B.

The process may include forming a recycle loop with $C_5$ olefin dehydrogenation reactor 20a and $C_5$ diolefin extractive distillation unit 10a, as shown in FIG. 2C. For example and without limitation, $C_5$ diolefin extractive distillation unit 10a may be a preexisting $C_5$ diolefin extractive distillation unit 10a that is not arranged in a recycle loop with a dehydrogenation reactor. Forming the recycle loop may include arranging $C_5$ olefin dehydrogenation reactor 20a relative to $C_5$ diolefin extractive distillation unit 10a such that the recycle loop is characterized in that $C_5$ olefin dehydrogenation reactor 20a is adapted to receive at least a portion of raffinate stream 18a (e.g., second portion 22a) from $C_5$ diolefin extractive distillation unit 10a. First portion 21a may be purged. Also, forming the recycle loop may include arranging $C_5$ olefin dehydrogenation reactor 20a relative to $C_5$ diolefin extractive distillation unit 10a such that the recycle loop is characterized in that $C_5$ diolefin extractive distillation unit 10a is adapted to receive dehydrogenation product stream 26a from $C_5$ olefin dehydrogenation reactor 20a. Steam 23a may be provided to $C_5$ olefin dehydrogenation reactor 20a, and hydrogen and offgas 24a may be removed from $C_5$ olefin dehydrogenation reactor 20a.

Adapting $C_5$ olefin dehydrogenation reactor 20a to receive second portion of raffinate stream 22a from $C_5$ diolefin extractive distillation unit 10a may include providing fluid communication between an upstream portion of $C_5$ olefin dehydrogenation reactor 20a and a downstream portion of $C_5$ diolefin extractive distillation unit 10a. Adapting $C_5$ diolefin extractive distillation unit 10a to receive dehydrogenation product stream 26a from $C_5$ olefin dehydrogenation reactor 20a may include providing fluid communication between a downstream portion of $C_5$ olefin dehydrogenation reactor 20a and an upstream portion of $C_5$ diolefin extractive distillation unit 10a. Fluid communication may be provided by conduits (e.g., pipes) or any other manner known to those of ordinary skill in the art.

After modifying $C_5$ diolefin extractive distillation unit 10a, the process for increasing the amount of $C_5$ diolefin obtained from raw $C_5$ stream 12a may be performed. For example, combined stream 13a may be subjected to extractive distillation in modified $C_5$ diolefin extractive distillation unit 100a having $C_5$ olefin dehydrogenation reactor 20a in a recycle loop therewith. The extractive distillation, dehydrogenation, and recycling may be performed in the manner described in more detail above with reference to FIG. 1.

Figure 3:
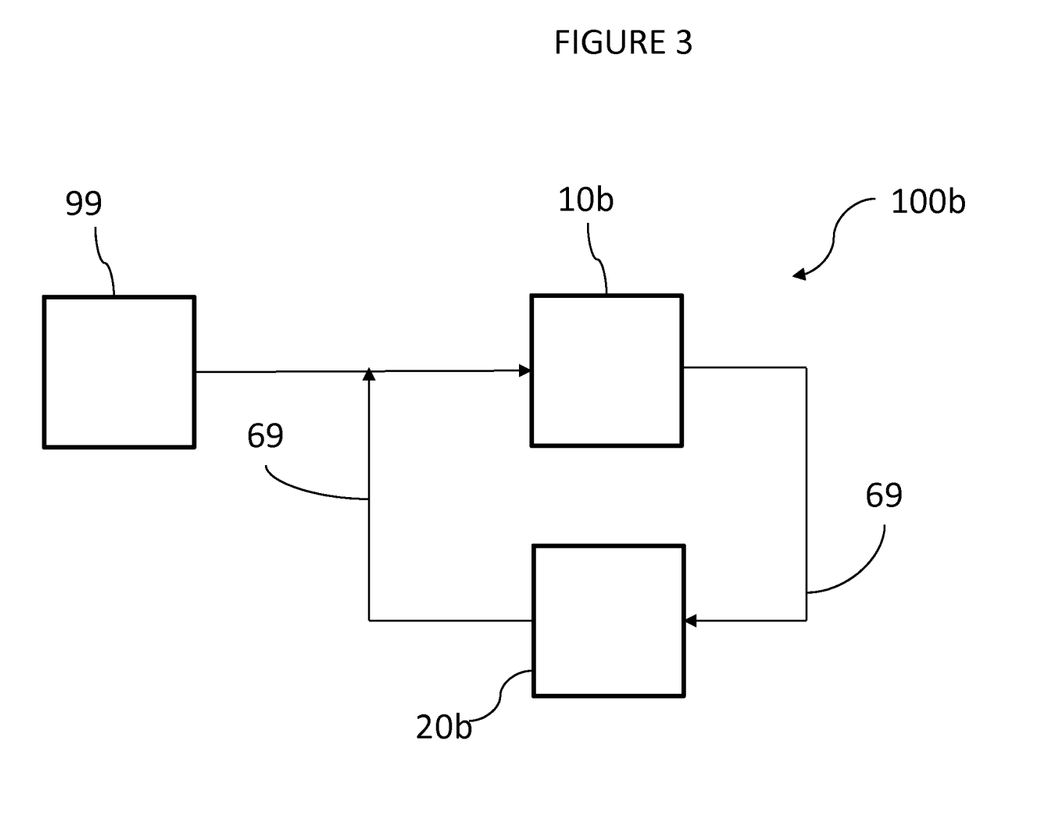
FIG. 3 depicts a system in accordance with certain embodiments of the present disclosure.

Certain embodiments of the present disclosure relate to a system for increasing an amount of $C_5$ diolefin obtained from a raw $C_5$ stream. As depicted in FIG. 3, system 100b may include $C_5$ diolefin extractive distillation unit 10b, which may be an extractive distillation column. The system may include $C_5$ olefin dehydrogenation reactor 20b. $C_5$ olefin dehydrogenation reactor 20b and $C_5$ diolefin extractive distillation unit 10b may be arranged to form recycle loop 69. Recycle loop 69 may be characterized in that $C_5$ olefin dehydrogenation reactor 20b is adapted to receive at least a portion of a raffinate stream from $C_5$ diolefin extractive distillation unit 10b, and $C_5$ diolefin extractive distillation unit 10b is adapted to receive a dehydrogenation product stream from $C_5$ olefin dehydrogenation reactor 20b, as described in greater detail above with reference to FIGS. 1, 2A, 2B and 2C. In some embodiments, system 100b is downstream of a cracking unit 99, such as a steam cracker or catalytic cracker. System 100b may be used to implement the process described above with reference to FIG. 1.

Figure 4:
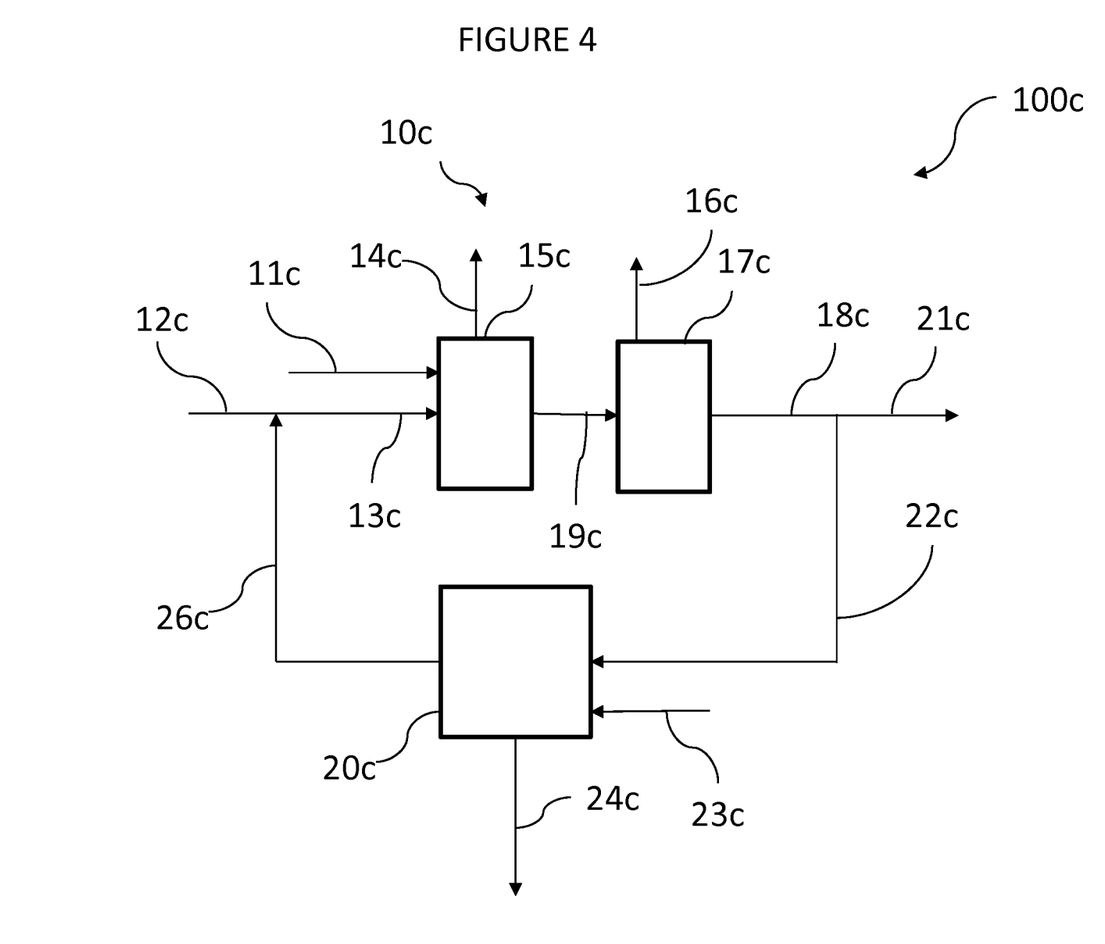
FIG. 4 depicts another system in accordance with certain embodiments of the present disclosure.

FIG. 4 depicts another system for increasing an amount of $C_5$ diolefin obtained from a raw $C_5$ stream in accordance with certain embodiments. System 100c may operate in substantially the same manner as systems 100, 100a, and 100b as described above with reference to FIGS. 1, 2C, and 3. System 100c includes $C_5$ diolefin extractive distillation unit 10c. $C_5$ diolefin extractive distillation unit 10c includes multiple extractive distillation columns arranged in series, including first extractive distillation column 15c and second extractive distillation column 17c. Within first extractive distillation column 15c, raw $C_5$ stream 12c may contact solvent 11c and undergo extractive distillation, forming first cut 14c (e.g., isoprene) as a top stream and bottoms stream 19c.

Bottoms stream 19c may enter second extractive distillation column 17c and undergo extractive distillation, forming second cut 16c (e.g., piperylene) as a top stream and raffinate stream 18c.

First portion of raffinate stream 21c may be purged from the process, and second portion of raffinate stream 22c may be subjected to dehydrogenation in $C_5$ olefin dehydrogenation reactor 20c in the presence of steam 23c and catalyst, forming hydrogen and offgas 24c and dehydrogenation products stream 26c.

Dehydrogenation products stream 26c may be recycled to extractive distillation unit 10c, such as by combining with raw C5 stream 12c to form combined stream 13c.

The disclosure having been generally described, the following examples show particular embodiments of the disclosure. It is understood that the example is given by way of illustration and is not intended to limit the specification or the claims. All compositions percentages given in the examples are by weight unless stated otherwise.

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A process comprising:
    forming a crude $C_{5+}$ stream in a cracker, the crude $C_{5+}$ stream comprising diolefins, olefins, paraffins, and combinations thereof,
    separating a raw $C_5$ stream from the crude $C_{5+}$ stream by fractional distillation, the raw $C_5$ stream comprising $C_5$ olefins, $C_5$ paraffins, and $C_5$ diolefins,
    feeding the raw $C_5$ stream directly to an extractive distillation unit and subjecting the raw $C_5$ stream to extractive distillation using a solvent that consists of dimethylformamide, furfural, N-methyl-2-pyrrolidone, or dimethylacetamide to form a first cut containing isoprene, a second cut containing greater than 99 percent by weight piperylene, and a raffinate stream containing $C_5$ olefins,
    wherein the extractive distillation unit is disposed upstream of a dehydrogenation reactor,
    subjecting at least a first portion of the raffinate stream to dehydrogenation in the dehydrogenation reactor to form a dehydrogenation product stream containing $C_5$ diolefins; and
    recycling the dehydrogenation product stream from the dehydrogenation reactor back to the extractive distillation unit.

2. The process of claim 1, wherein a second portion of the raffinate stream is purged.

3. The process of claim 2, wherein the second portion of the raffinate stream further includes paraffins and naphthenes.

4. The process of claim 1, wherein the dehydrogenation product stream further includes paraffins and naphthenes.

5. The process of claim 1, wherein a content of $C_5$ diolefins, by weight, in a combination of the raw $C_5$ stream and the dehydrogenation product stream is not less than a content of $C_5$ diolefins, by weight, in the raw $C_5$ stream alone.

6. The process of claim 1, wherein recycling the dehydrogenation product stream to the extractive distillation unit comprises combining the dehydrogenation product stream with the raw $C_5$ stream upstream of the extractive distillation unit, or wherein the dehydrogenation product stream and the raw $C_5$ stream are separately fed into the extractive distillation unit.

7. A process for modifying a $C_5$ diolefin extractive distillation unit comprising:
    receiving a pyrolysis gasoline feed stream containing $C_5$ diolefins,
    introducing the pyrolysis gasoline feed stream to the $C_5$ diolefin extractive distillation unit and subjecting the pyrolysis gasoline feed stream to extractive distillation using a solvent that consists of dimethylformamide, furfural, N-methyl-2-pyrrolidone, or dimethylacetamide to form a first top distillation cut containing isoprene, a second top distillation cut containing piperylene, and a raffinate stream containing $C_5$ olefins,
    wherein the $C_5$ diolefin extractive distillation unit comprises a first extractive distillation column and a second extractive distillation column, wherein the first extractive distillation column receives the pyrolysis gasoline feed stream and produces the first top distillation cut and a bottoms stream, and the second extractive distillation column receives the bottoms stream from the first extractive distillation column and produces the second top distillation cut and the raffinate stream, and
    forming a recycle loop with a $C_5$ olefin dehydrogenation reactor and the $C_5$ diolefin extractive distillation unit,
    wherein the recycle loop is characterized in that the dehydrogenation reactor receives at least a first portion of a raffinate stream from the extractive distillation unit, the first extractive distillation column further receives a product stream from the dehydrogenation reactor, and the extractive distillation unit is disposed upstream of the dehydrogenation reactor.

8. The process of claim 7,
    wherein the raffinate stream includes $C_5$ olefins, $C_5$ diolefins, paraffins, naphthenes, diolefins other than $C_5$ diolefins, and olefins other than $C_5$ olefins.

9. The process of claim 7, wherein a second portion of the raffinate stream is purged.

10. The process of claim 9, wherein the second portion of the raffinate stream further includes paraffins and naphthenes.

11. The process of claim 7, wherein a content of $C_5$ diolefins, by weight, of a combination of the pyrolysis gasoline feed stream and the dehydrogenation product stream is not less than a content of $C_5$ diolefins, by weight, in the pyrolysis gasoline feed stream alone.

12. The process of claim 7, wherein the extractive distillation unit receives a combination of the dehydrogenation product stream and the pyrolysis gasoline feed stream, or wherein the extractive distillation unit receives the dehydrogenation product stream and the pyrolysis gasoline feed stream separately.

13. A process comprising:
    providing an extractive distillation unit comprising a first extractive distillation column and a second extractive distillation column in series, passing a feed containing $C_5$ diolefins from a cracking process and a dehydrogenation product stream containing $C_5$ diolefins directly to the first extractive distillation column to produce a first top distillation cut including isoprene and a bottoms stream, passing the bottoms stream to the second extractive distillation column to produce a second top distillation cut including piperylene and a raffinate stream containing $C_5$ olefins subjecting at least a portion of the raffinate stream containing $C_5$ olefins from the extractive distillation unit to dehydrogenation in a dehydrogenation reactor to form a dehydrogenation product stream containing $C_5$ diolefins, and recycling the dehydrogenation product stream to the extractive distillation unit, wherein the extractive distillation unit is disposed upstream of the dehydrogenation reactor and the extractive distillation unit uses a solvent that consists of acetonitrile, dimethylformamide, furfural, N-methyl-2-pyrrolidone, acetone, or dimethylacetamide.

14. The process of claim 1, wherein the raffinate stream contains $C_5$ olefins, $C_5$ diolefins, paraffins, naphthenes, diolefins other than $C_5$ diolefins, and olefins other than $C_5$ olefins.

* * * * *